US00PP11073P

United States Patent [19]

Ackerman

[11] Patent Number: Plant 11,073

[45] Date of Patent: Sep. 28, 1999

[54] RASPBERRY PLANT NAMED 'PS-1070'

[75] Inventor: Stephen M. Ackerman, Salinas, Calif.

[73] Assignees: Plant Sciences, Inc.; Berry R & D, Inc., both of Watsonville, Calif.

[21] Appl. No.: 09/021,894

[22] Filed: Feb. 11, 1998

[51] Int. Cl.[6] ..... A01H 5/00

[52] U.S. Cl. ..... Plt./204

[58] Field of Search ..... Plt./204

[56] References Cited

U.S. PATENT DOCUMENTS

P.P. 9,653 10/1996 Wilhelm et al. ..... Plt./204

*Primary Examiner*—Howard J. Locker
*Assistant Examiner*—Wendy A Baker
*Attorney, Agent, or Firm*—Christie, Parker & Hale, LLP

[57] ABSTRACT

This invention relates to a new and distinct fall bearing red raspberry variety named 'PS-1070' which is capable of producing fruit on first year primocanes, and both floricanes and primocanes in subsequent years. The new variety is particularly characterized by its early July primocane production. The fruit is medium to small in size, light in color, and round in shape. The fruit is of very good quality adapted well to the fresh fruit market with only a slight tendency to darken after harvest. The plant is moderately-vigorous with dense foliage. The leaves are relatively medium to large in size with an occasional raised mid vein and slight downward cupping.

4 Drawing Sheets

BACKGROUND OF THE INVENTION

The present invention relates to a new and distinct fall-bearing red raspberry variety which is the result of a cross between the variety designated as 'PS-114' (U.S. Plant Pat. No. 7,451) and 'Heritage' an unpatented variety. The new variety is botanically known as *Rubus idaeus* and the varietal name is 'PS-1070'.

SUMMARY OF THE INVENTION

This variety of raspberry resulted from a breeding program with the objective of developing new and distinct raspberry varieties. The seedling resulting from the aforementioned cross was asexually propagated by dormant canes in a nursery located in Santa Cruz County, Calif., and was subsequently selected from a controlled breeding plot near Watsonville, Calif. in 1990. After its selection, the new variety was further asexually propagated in Santa Cruz County, Calif. by dormant canes, roots and non-dormant root shoot cutting and extensively tested over the next several years in fruiting fields near Watsonville, Calif. This propagation and reproduction has demonstrated that the combination of traits disclosed herein as characterizing the new variety are fixed and remain true to type through successive generations of asexual reproduction.

BRIEF DESCRIPTION OF ILLUSTRATIONS

The accompanying description and photographs describe typical specimens of the new variety at various stages of development as nearly true as it is possible to make in color reproduction of these characters. Phenotypic expression may vary with differences in growth, environmental, and cultural conditions. Color terminology follows the Munsell Book of Colors, Munsell Color, Baltimore, Md. (1976).

DESCRIPTION OF THE NEW VARIETY

Figure 1:
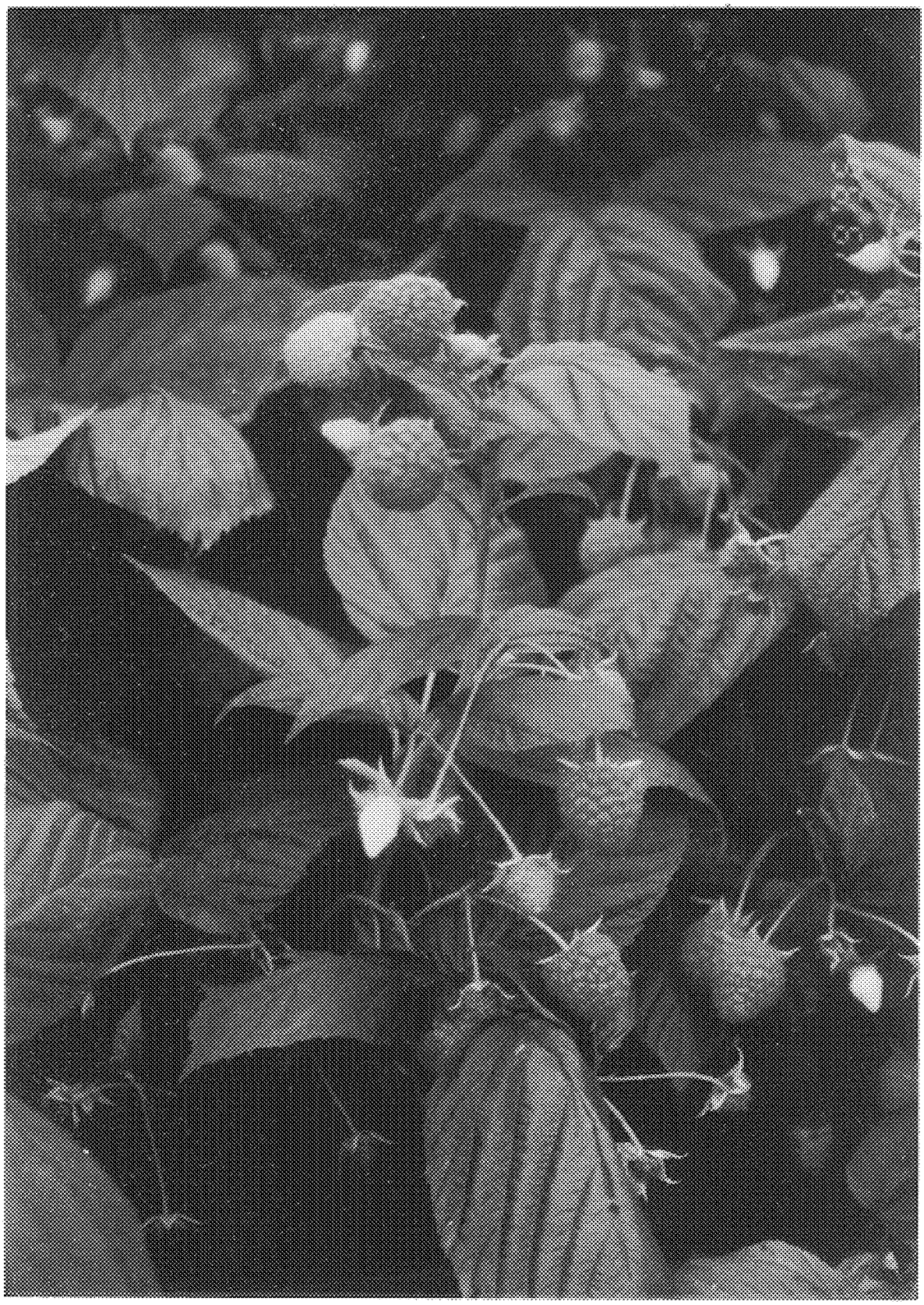
FIG. 1 shows a typical fruiting terminal and developmental stages from flower to mature fruit.
Figure 2:
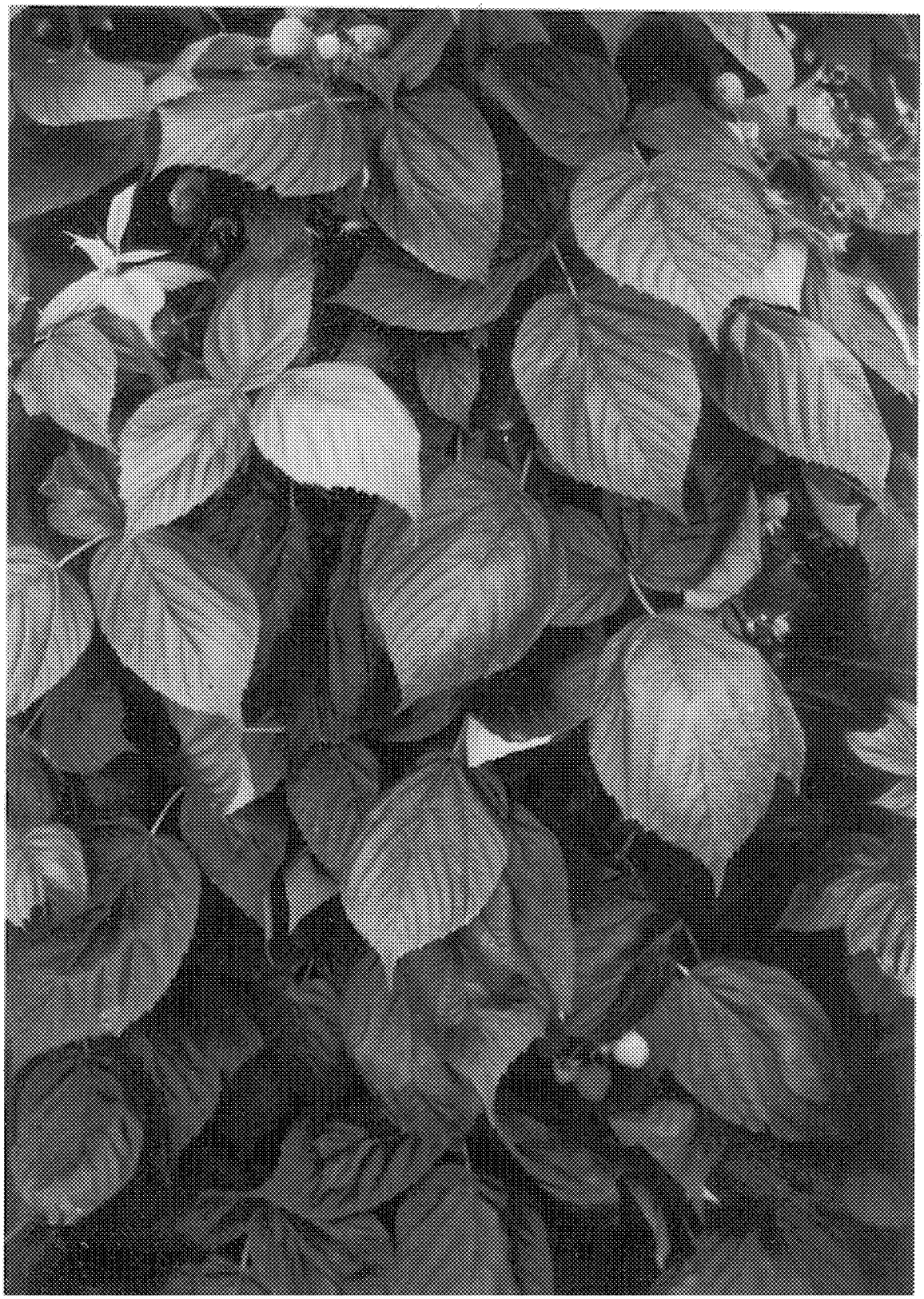
FIG. 2 shows plant foliage depicting typical shape cupping and venation.
Figure 3:
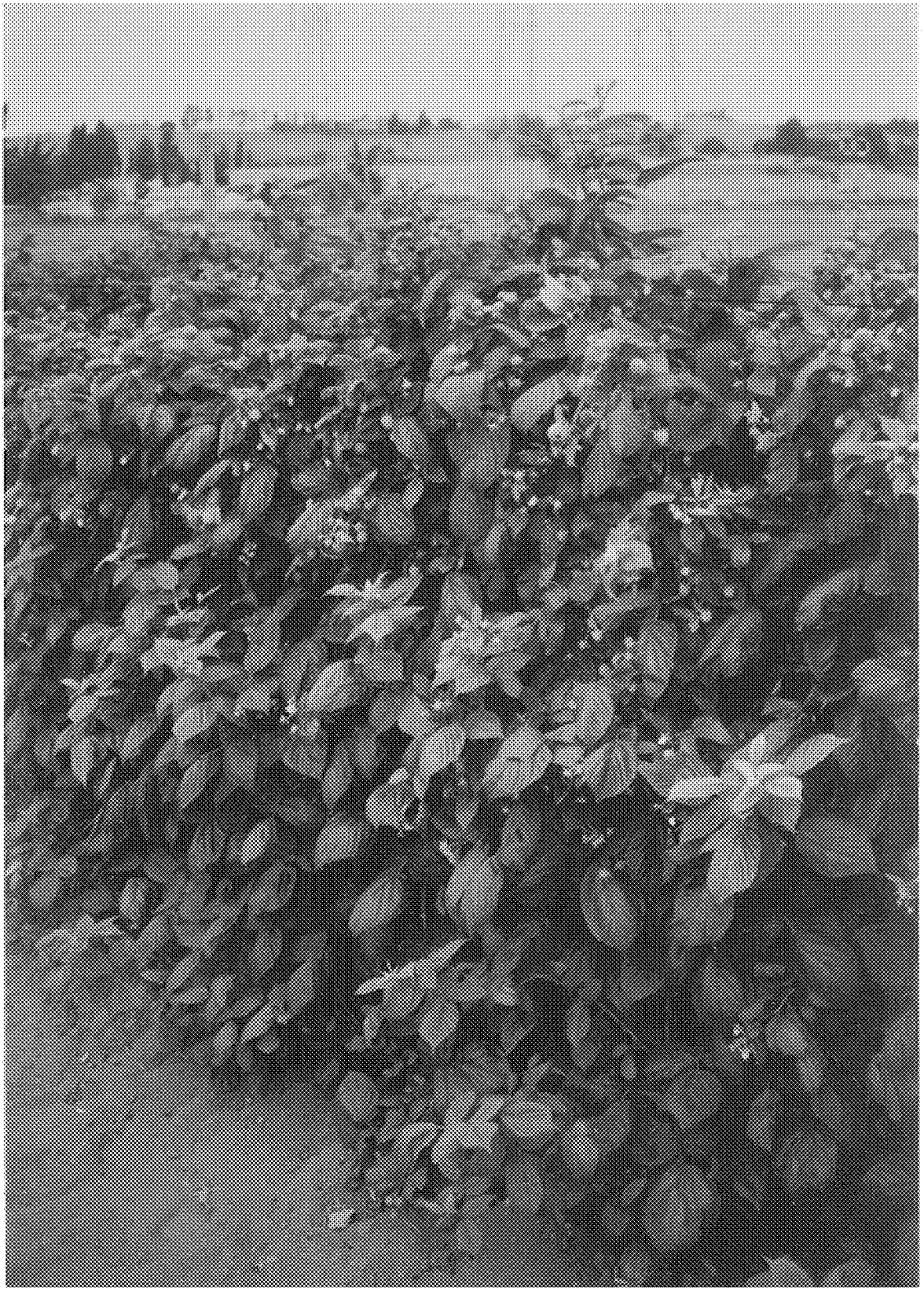
FIG. 3 shows typical plant growth habit and fruiting characteristics.
Figure 4:
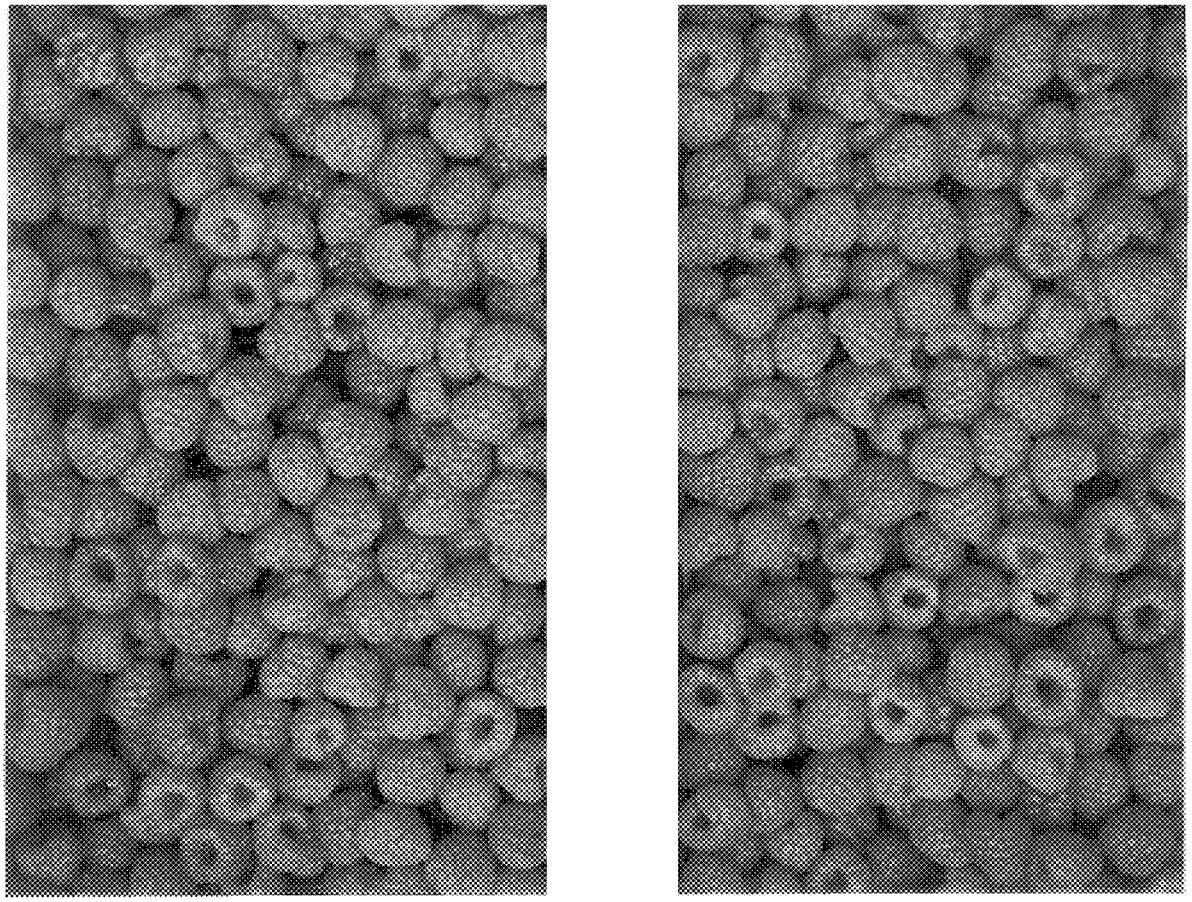
FIG. 4 shows typical fruit.

'PS-1070' is primarily adapted to the climate and growing conditions of the central coast of California. This region provides the necessary year-round temperatures required to produce a strong vigorous plant, and to remain in fruit production from about July through November on primocanes and, in the ensuing year from about May through July on floricanes. The nearby Pacific ocean provides humidity and cool temperatures to maintain fruit quality during the summer production months.

'PS-1070' is a moderately vigorous plant with dense deciduous foliage when provided with optimum chilling in the nursery propagation fields prior to being dug, and artificial cold storage prior to being planted. The plant of the new variety is shorter 'PS-1049' claimed in the U.S. Plant Pat. No. 10,142, yet similar in height to 'PS-127' (U.S. Plant Pat. No. 7,437) with a lighter primocane color, smaller basal diameter and shorter fruiting laterals than both 'PS-1049' and 'PS-127'. A moderate number of medium textured thorns are present on the mature canes of 'PS-1070', lighter i texture than 'PS-1049' and heavier than 'PS-127'. Table 1 summarizes primocane characteristics of 'PS-1070', 'PS-1049' and 'PS- 127'.

The foliage of the new variety is slightly lighter in color than both 'PS-1049' and 'PS-127'. Leaf shape is less rounded yet similarly cupped at the margins as compared to 'PS-127'. The leaves are generally smaller than 'PS-1049' and larger than 'PS-127'. Terminal leaflets have a slightly raised mid vein, less prominent than 'PS-1049'. Table 2 summarizes foliage comparisos characteristics for 'PS-107', 'PS- 1049' and 'PS- 127'.

'PS-1070' is capable of long season fruit production with fruit of acceptable size and excellent quality during the entire season. Primocane fruit production of 'PS-1070' begins as early as late June to early July, earlier than both 'PS-1049' and 'PS-127' with a heavier July-August crop than both 'PS-1049' and 'PS-127'. 'PS-1070' peaks from about early to mid August, earlier than both 'PS-1049' and 'PS-127'. Primocane production of 'PS-1070' may continue into November if rains and cold temperatures do not prevent the harvest with a lighter total primocane yield than 'PS-1049'. Table 3 summarizes fruit production characteristics for 'PS-1070'. 'PS-1049' and 'PS-127'.

Floricane fruit production of 'PS-1070' begins early to mid May, later than both 'PS-1049' and 'PS-127' with a lighter May crop than both. 'PS-1070' peaks from about early to mid June, earlier than 'PS-1049' and later than 'PS-127' with lighter July yields than 'PS-1049' and a lighter total floricane yield than both 'PS-1049' and 'PS-127'. Primocane and floricane season average fruit of 'PS-1070' is also smaller than both 'PS-1049' and 'PS-127'.

The fruit of 'PS-1070' is more uniformly shaped as compared to 'PS-127' and more rounded in shape than both. 'PS-1070' has better overall appearance, firmness and gloss than 'PS-127'. Table 5 summarizes fruit quality performance ratings. The fruit of 'PS-1070' is noticeably lighter in color than both 'PS-1049' and 'PS- 127'. Druplets are more uniformly sized and arranged around the surface of the berry as compared to 'PS-127'. Seeds are also gnerally smaller in size than both 'PS-1049' and 'PS-127'. Table 4 summarizes fruit characteristics for 'PS-1070', 'PS-1049' and 'PS-127'.

TABLE 1

Comparison of mature primocane plant characteristics of 'PS-1070', 'PS-1049' and 'PS-127' from Watsonville, California, August 21, 1996.

| Character | 'PS-1070' | 'PS-1049' | 'PS-127' |
|---|---|---|---|
| Munsell Color primocane | 5GY 6/6 to 5GY 7/6 | 5GY 7/4 to 5GY 6/4 | 5GY 7/4 to 5GY 6/4 |
| Primocane Length mean (m) | 1.5 | 1.7 | 1.4 |
| Lateral Length mean (cm) | 37.7 | 47.9 | 66.9 |
| Primocane Basal diameter mean (mm) | 9.3 | 12.0 | 10.9 |
| Primocane Internode length mean (cm) | 5.5 | 4.4 | 4.0 |
| Thorn Length mean (mm) | 1.8 | 2.0 | 1.4 |

TABLE 2

Comparison of mature leaf characteristics of 'PS- 1070', 'PS-1049' and 'PS-127' from Watsonville, California, August 21, 1996.

| Character | 'PS-1070' | 'PS-1049' | 'PS-127' |
|---|---|---|---|
| Munsell Leaf Color (upper surface) | 5GY 3/4 to 5GY 3/6 | 7.5GY 3/4 to 7.5GY 4/4 | 7.5GY 3/4 to 7.5GY 2/4 |
| Terminal Leaflet length mean (cm)* | 13.6 | 14.0 | 12.1 |
| Terminal Leaflet width mean (cm)* | 9.3 | 10.0 | 10.0 |
| Terminal Leaflet ratio (L/W)* | 1.46 | 1.39 | 1.21 |
| Petiole Length mean (cm) | 4.5 | 5.2 | 5.0 |
| Petiole Width mean (mm) | 2.8 | 2.8 | 3.2 |
| Petiolule Length mean (mm)** | | | |

*Terminal leaflets measurements are taken from a 3 leaflet leaf.
**Petiolule length between the terminal leaflet and the adjacent lateral leaflets of a 3 leaflet leaf.

TABLE 3

1992–1996 average market fruit yield and fruit size characteristics from plants harvested from July through November (primocane) and May through July (floricane) of 'PS-1070' compared with 'PS-1049' and 'PS-127' dug Mid-December and planted Mid-January in Watsonville, California.

| Character | 'PS-1070' | 'PS-1049' | 'PS-127' |
|---|---|---|---|
| Primocane Yield July–August gm/pl | 1000 | 698 | 453 |
| Primocane Yield total gm/pl | 1490 | 1864 | 1361 |
| Floricane Yield May gm/pl | 246 | 378 | 537 |
| Floricane Yield July gm/pl | 193 | 454 | 138 |
| Floricane Yield total gm/pl | 1173 | 1573 | 1345 |
| Average Primocane fruit size mean (gms) | 2.5 | 2.7 | 2.7 |
| Average Floricane fruit size mean (gms) | 2.1 | 2.2 | 2.3 |

TABLE 4

Comparison of mature fruit characteristics of 'PS-1070', 'PS-1049' and 'PS-127' from Watsonville, California, August 13, 1996.

| Character | 'PS-1070' | 'PS-1049' | 'PS-127' |
|---|---|---|---|
| Munsell Color fresh fruit | 7.5R 4/10 to 7.5R 3/10 | 5R 3/6 to 5R 3/8 | 7.5R 3/8 to 7.5R 3/10 |
| Fruit Length mean (cm) | 1.7 | 1.9 | 2.0 |
| Fruit Width mean (cm)* | 1.8 | 1.8 | 1.9 |
| Seeds per Berry mean | 79 | 91 | 70 |
| Seed Weight mean (mgs)** | 1.36 | 1.45 | 1.75 |

*Width was measured across the widest part of the berry, typically across the shoulders.
**Seed weight is measured after drying for 48 hours at room temperature.

TABLE 5

Comparison of Primocane fruit quality characteristics of 'PS-1070', 'PS-1049' and 'PS-1027'*

| Character | 'PS-1070' | 'PS-1049' | 'PS-127' |
|---|---|---|---|
| Skin Firmness | 8.7 | 8.7 | 8.1 |
| Fruit Appearance | 7.9 | 8.2 | 7.0 |
| Fruit Floss | 7.1 | 7.0 | 6.7 |

*Results are an average from 3 years of fruit quality tests performed from August through October of 1993 to 1995 in Watsonville, California. Ratings are based on a scale from 1–10; the higher the rating the stronger the skin and more attractive and glossy the berry.

SPECIFIC DESCRIPTION OF THE NEW VARIETY

The following further describes 'PS-1070', including the variety's morphological, electrophoretic, pest and disease reaction characteristics. This detailed description is based on observations taken during the spring and summer of 1996 in fruiting fields near Watsonville, Calif. Some characteristics were rated at different times in which case the date of the evaluation is listed. These measurements and ratings were made from plants dug from a nursery located in Santa Cruz County, Calif. in November 1995 and planted as dormant root stocki in December 1995. The phenotypic characteristics of the new variety may vary slightly, depending upon variations in environmental factors, including weather (temperature, humidity and light intensity), day length, soil type and location without any change in the genotype of the plant. 'PS-1070' has not been observed under all possible environmental conditions. It has also not been tested for winter hardiness.

FRUIT CHARACTERISTICS

The fresh fruit of 'PS-1070' is moderately glossy and light red in color at maturity, color near 7.5R 4/10 to 7.5R 3/10. Mature fruit has a tendency to darken slightly after harvest to a color near 5R 3/8 to 5R 3/10. The mature fruit is very firm with good appearance. Table 5 summarizes fruit quality characteristics of 'PS-1070'. At maturity, the fruit is weakly attached to the receptacle and easily separated from the receptacle. The fruit cavity is medium to small in size and funnel shaped. The receptacle is conic in shape tapering to a blunt tip and semi-smooth in texture. The fruit possesses acceptable flavor and very good shipping qualities desirable for the fresh fruit markets.

The fruit is medium to small in size and charactertistically round in shape. The fruit is typically wider than long with a moderate number of small to medium sized druplets. Table 4 summarizes fruit characteristics of 'PS-1070'. The druplets are generally of uniform size and shape around the berry. The druplets forming the berry collar at the open end fit tightly together forming a uniform ring of druplets.

PLANT CHARACTERISTICS

Primocanes of 'PS-1070' are moderately vigorous, of erect habit, with dense deciduous foliage. The plant crown produces from 2 to 8 primocane shoots per crown during the growing season and fruits on approximately the upper ⅓ of the cane. Mature primocanes are medium to small in diameter, average from about 7.0 mm to 10.0 mm at the base to about 7.0 mm to 9.0 mm at approximately mid cane. Internodes are of medium length averaging about 4.0 cm to 7.0 cm in length at approximately the central ⅓ of the cane. Table 1 summarizes primocane plant characteristics of 'PS-1070'. Mature primocanes are light green in color, color near 5GY 6/6 to 5GY 7/6 and produce many erect lateral branches on the upper third of the cane. A moderate number of medium textured thorns are also9 present on the mature canes. The Thorn tips are held in a horizontal position relative to the cane axis. The basal thorn color is similar to the cane, color near 5GY 6/6 to 5GY 7/6 with a reddish purple tip, color near 7.5RP 4/6.

Floricanes are light brown in color, color near 10YR 5/4 to 10YR 6/4 with a moderate number of lateral branches per cane. Floricane length is from 1 to 1.3 meters.

FOLIAGE CHARACTERISTICS

Mature leaves are a medium greenish yellow in color, color near 5GY 3/4 to 5GY 3/6 on the upper surface and a pale greenish yellow color, color near 5GY 7/2 to 5GY 6/2 on the underside. Leaves are compound and nearly always with 3 leaflets per leaf. The terminal leaflets are cordate in shape tapering to an acuminate tip and doubly serrated. Serrations are small, shallow and present on all leaflets. Terminal leaflets are also medium to large in size and longer than wide as described by the length/width ratio. Table 2 summarizes foliage characteristics of 'PS-1070'. Lateral leaflets are opposite and slightly overlapping. The upper surface of the leaf is moderately glossy. Leaf veins are moderate with an occasionally raised mid vein and slight downward cupping. Petioles are a light greenish yellow color, color near 5GY 8/6 to 5GY 6/4 medium to short in length and of medium thickness with a non waxy surface. Thorns are present and of medium texture with the tips held in a horizontal position to the surface.

FLOWERS

Flowers are white, medium to small in size, self-fertile and have 5 to 6 petals per flower. Petals are 5–7 mm long and 3–5 mm wide. Each flower produces ample pollen for good pollination. Flowers and fruit are well exposed for easy access to picking.

PEST AND DISEASE REACTIONS

The new variety may not be resistant to any of the known insects and diseases common in California. It has shown to be slightly susceptible to late yellow rust, cane botrytis, fruit rot, and powdery mildew. It has not been tested for resistance to any of the root rot or virus complexes.

ISOZYME IN LEAF EXTRACT

Studies of protein polymorphism in Rubus by the starch gel electrophoresis method were carried out to characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5.3.1.9), phosphoglucomutase (PGM: EC 2.7.5.1).

The testing used both field and greenhouse grown plant material, all grown in Watsonville, Calif. Newly mature leaves (0.5 g fresh weight) from the growing tips of the canes were used. Samples were collected in the morning, held at 4° C. and analyzed within six hours.

The tissue preparation, extraction and staining are as reported in S. Arulsekar and D. E. Parfitt, "Isozyme Analysis Procedures for Stone Fruits, Almond, Grape, Walnut, Pistachio, and Fig", HortScience 21(4): 928–933.

Following electrophoresis, the gel was sliced and stained for each enzyme system. Banding patterns were interpreted as they developed, and gel sl ices were fixed in 50% glycerol.

I claim:

1. A new and distinct red raspberry plant of the variety substantially as shown and described.

* * * * *